(12) United States Patent
Widge et al.

(10) Patent No.: US 11,351,379 B2
(45) Date of Patent: Jun. 7, 2022

(54) SYSTEMS AND METHODS FOR CONTROLLING SYNCHRONY IN A PLURALITY OF BRAIN REGIONS

(71) Applicant: The General Hospital Corporation, Boston, MA (US)

(72) Inventors: Alik S. Widge, Somerville, MA (US); Meng-Chen Lo, Cambridge, MA (US); Ethan Blackwood, Somerville, MA (US)

(73) Assignee: The General Hospital Corporation, Boston, MA (US)

( * ) Notice: Subject to any disclaimer, the term of this patent is extended or adjusted under 35 U.S.C. 154(b) by 28 days.

(21) Appl. No.: 16/762,563

(22) PCT Filed: Nov. 13, 2018

(86) PCT No.: PCT/US2018/060624
§ 371 (c)(1),
(2) Date: May 8, 2020

(87) PCT Pub. No.: WO2019/094886
PCT Pub. Date: May 16, 2019

(65) Prior Publication Data
US 2020/0360695 A1 Nov. 19, 2020

Related U.S. Application Data

(60) Provisional application No. 62/584,991, filed on Nov. 13, 2017.

(51) Int. Cl.
*A61N 1/36* (2006.01)
*A61N 1/05* (2006.01)
*A61N 1/372* (2006.01)

(52) U.S. Cl.
CPC ....... *A61N 1/36139* (2013.01); *A61N 1/0534* (2013.01); *A61N 1/36178* (2013.01);
(Continued)

(58) Field of Classification Search
CPC .............. A61N 1/36139; A61N 1/0534; A61N 1/36178; A61N 1/37211; A61N 1/36067; A61N 1/36082
See application file for complete search history.

(56) References Cited

U.S. PATENT DOCUMENTS

| | | | |
|---|---|---|---|
| 2012/0271374 A1* | 10/2012 | Nelson | A61N 1/0534 607/45 |
| 2016/0220836 A1 | 8/2016 | Parks | |
| 2017/0128729 A1 | 5/2017 | Netoff et al. | |

FOREIGN PATENT DOCUMENTS

| | | |
|---|---|---|
| WO | 2017021661 A1 | 2/2017 |
| WO | 2017223430 A1 | 12/2017 |

OTHER PUBLICATIONS

Benchenane et al., Oscillations in the Prefrontal Cortex: A Gateway to Memory and Attention, Current Opinion in Neurobiology, 2011, 21(3):475-485.

(Continued)

*Primary Examiner* — Paula J Stice
(74) *Attorney, Agent, or Firm* — Quarles & Brady LLP

(57) ABSTRACT

A method for controlling synchrony in a plurality of brain regions of a subject includes receiving signals from a source region of the subject's brain, determining at least one phase of the signals from the source region in a predetermined frequency band and delivering at least one stimulation pulse to at least one target region of the subjects brain based on the at least one phase of the signals from the source region to synchronize oscillations of the source region and the at least one target region.

23 Claims, 7 Drawing Sheets

(52) U.S. Cl.
CPC ...... *A61N 1/37211* (2013.01); *A61N 1/36067* (2013.01); *A61N 1/36082* (2013.01)

(56) References Cited

OTHER PUBLICATIONS

Blackwood et al., Continuous Phase Estimation for Phase-Locked Neural Stimulation Using an Autoregressive Model for Signal Prediction, In 2018 40th Annual International Conference of the IEEE Engineering in Medicine and Biology Society (EMBC), pp. 4736-4739.
Buschman et al., Serial, Covert Shifts of Attention During Visual Search are Reflected by the Frontal Eye Fields and Correlated with Population Oscillations, Neuron, 2009, 63(3):386-396.
Chen et al., Real-Time Brain Oscillation Detection and Phase-Locked Stimulation Using Autoregressive Spectral Estimation and Time-Series Forward Prediction, IEEE Transactions on Biomedical Engineering, 2011, 60(3):753-762.
Cho et al., Gamma Rhythms Link Prefrontal Interneuron Dysfunction with Cognitive Inflexibility in Dlx5/6+/− Mice, Neuron, 2015, 85(6):1332-1343.
Hoy et al., The Effect of Transcranial Direct Current Stimulation on Gamma Activity and Working Memory in Schizophrenia, Psychiatry Research, 2015, 228(2):191-196.
Huang et al., On Instantaneous Frequency, Advances in Adaptive Data Analysis, 2009, 1(2):177-229.
Karalis et al., 4-Hz Oscillations Synchronize Prefrontal-Amygdala Circuits During Fear Behavior, Nature Neuroscience, 2016, 19(4):605-612.
Likhtik et al., Prefrontal Entrainment of Amygdala Activity Signals Safety in Learned Fear and Innate Anxiety, Nature Neuroscience, 2014, 17(1):106-113.
Likhtik et al., Amygdala-Prefrontal Interactions in (Mal) Adaptive Learning, Trends in Neurosciences, 2015, 38(3):158-166.
Malone Jr et al., Deep Brain Stimulation of the Ventral Capsule/Ventral Striatum for Treatment-Resistant Depression, Biological Psychiatry, 2009, 65(4):267-275.
Mathalon et al., Neural Oscillations and Synchrony in Brain Dysfunction and Neuropsychiatric Disorders: It's About Time, JAMA Psychiatry, 2015, 72(8):840-844.
Meidahl et al., Adaptive Deep Brain Stimulation for Movement Disorders: The Long Road to Clinical Therapy, Movement Disorders, 2017, 32(6):810-819.
Milad et al., Fear Extinction as a Model for Translational Neuroscience: Ten Years of Progress, Annual Review of Psychology, 2012, 63:129-151.
Miller et al., Working Memory 2.0, Neuron, 2018, 100(2):463-475.
Philip et al., Low-Intensity Transcranial Current Stimulation in Psychiatry, American Journal of Psychiatry, 2017, 174(7):628-639.
Ramirez-Zamora et al., Evolving Applications, Technological Challenges and Future Opportunities in Neuromodulation: Proceedings of the Fifth Annual Deep Brain Stimulation Think Tank, Frontiers in Neuroscience, 2018, vol. 11, Article 734, 25 pages.
Siegel et al., Phase-Dependent Neuronal Coding of Objects in Short-Term Memory, Proceedings of the National Academy of Sciences, 2009, 106(50):21341-21346.
Siegle et al., Enhancement of Encoding and Retrieval Functions Through Theta Phase-Specific Manipulation of Hippocampus, eLife, 2014, 3:e03061, 18 pages.
Siegle et al., Open Ephys: An Open-Source, Plugin-Based Platform for Multichannel Electrophysiology, Journal of Neural Engineering, 2017, 14(4):045003, 13 pages.
Widge et al., Closing the Loop on Deep Brain Stimulation for Treatment-Resistant Depression, Frontiers in Neuroscience, 2018, vol. 12, Article 175, 10 pages.
PCT International Search Report and Written Opinion, PCT/US2018/060624, dated Jan. 11, 2019, 12 pages.

\* cited by examiner

SYSTEMS AND METHODS FOR CONTROLLING SYNCHRONY IN A PLURALITY OF BRAIN REGIONS

CROSS-REFERENCE TO RELATED APPLICATIONS

This application represents the national stage entry of PCT International Application No. PCT/US2018/050173 filed Sep. 10, 2018, which is based on, claims priority to, and incorporates herein by reference in their entirety U.S. Ser. No. 62/584,991 filed Nov. 13, 2017, and entitled "A Method to Synchronize Large-Scale Activity of Multiple Brain Regions By Oscillation-Locked Stimulation."

GOVERNMENT RIGHTS

This invention was made with government support under R21 MH109722-01A1 awarded by the National Institutes of Health. The government has certain rights in the invention.

BACKGROUND

The present disclosure relates generally to systems and methods for controlling brain activity and more particularly to systems and methods for synchronizing activity in a plurality of brain regions.

Patients suffering from mental and emotional conditions, such as post-traumatic stress disorder (PTSD), intellectual disability, autism, brain injury, depression, addiction, and others, can have severe impairments that lead to significant disability and lost productivity. Such brain disorders are thought to be caused by malfunctioning neural circuits. Often, psychiatric treatments fail to cure a substantial fraction of patients, who are then declared resistant to approved therapeutic interventions. At the core of the problem is the focus on historical diagnostic categories. The National Institute of Mental Health's (NIMH) Research Domain Criteria (RDoC) project aims to develop neuroscience-based classification schemes for diagnosis and treatment of neural circuitry dysfunction. Diagnostic and Statistical Manual (DSM) diagnoses are not neurobiologic entities, but are a historical checklist-based approach of clustering symptoms used to define hypothetical constructs or syndromes. Those syndromes may not align with underlying neurobiological dysfunction in neural circuitry and corresponding behavioral (functional) domains.

Thus, attempts have been made to treat mental and emotional disorders previously treated by psychiatrists using responsive brain stimulation systems. These approaches include stimulating a patient's brain based on brain activity or clinical features, using implantable, cortical and subcortical electrodes. In particular, there are a number of sites in the brain where stimulation has been applied in attempts to change a patient's emotional experiences. However, these responsive brain stimulation systems often have no proven biomarker. A biomarker may be a measurable indicator or signal from the brain or body representative of the symptoms of the illness being treated that indicates whether the symptoms have gotten better or worse. Without something reliable to sense, it is difficult for the responsive stimulator to respond accurately.

Further, neurologic and sensory-motor disorders also often involve dysfunctional connectivity within circuits. Parkinson's disease and other movement disorders involve abnormal oscillatory connectivity between cortex and basal ganglia. Spinal cord injury involves disconnection between motor cortex and descending control circuits.

Deep brain stimulation (DBS) is used to treat many conditions. For instance, DBS has been used to control symptoms, such as rigidity, slowed movement, tremors, and walking difficulties, in patients with Parkinson's. Other applications include epilepsy, chronic pain, obsessive compulsive disorder, depression, and others. The procedure involves implantation of an electrical stimulator into a defined area of a patient's brain, followed by delivery of high-frequency electrical impulses (e.g. up to 24 hours per day). In some applications, DBS may be unilateral or bilateral in the subthalamic nucleus (STN), internal capsule, deep cortex, or in the globus pallidus internus (GPi) depending on the observed symptoms and treatment plan.

Although the exact mechanism of action is not well understood, it is believed that electrical currents produced by DBS interfere with or block brain activity close to the activation site. As such, DBS affords a number of advantages over traditional ablative surgery including being less invasive, reversible, and allowing for bilateral stimulation. However, recent clinical trials using DBS for a variety of indications, most particularly depression, have failed. This is in part because current DBS technologies operate at single sites, rather than affecting circuit-level functions. By contrast, synchronized neural activity, detectable as coherent oscillation in the local field potential (LFP) from different brain regions, has been recognized as an important mechanism for communication between brain networks. Such oscillations are correlated to attention, learning and memory formation, help to coordinate brain networks involved in sensory-motor function, and are often impaired in psychiatric disorders including depression, post-traumatic stress disorder (PTSD), and obsessive compulsive disorder. Currently, there is a lack of methods and technologies to control inter-area oscillatory synchrony.

Therefore, given the above, there is a need for improved systems and methods for treating patients suffering from neurological conditions that involve circuit dysfunction or dys-connectivity.

SUMMARY

In accordance with one aspect of the disclosure, a method is provided for controlling synchrony in a plurality of brain regions of a subject that includes receiving signals from a source region of the subject's brain, determining at least one phase of the signals from the source region in a predetermined frequency band and delivering at least one stimulation pulse to a target region of the subject's brain based on the at least one phase of the signals from the source region to synchronize oscillations of the source region and the target region.

In accordance with another aspect of the disclosure, a method is provided for controlling synchrony in a plurality of brain regions of a subject that includes receiving signals from a source region of the subject's brain, determining at least one phase of the signals from the source region in a predetermined frequency band and delivering at least one stimulation pulse to a first target region of the subject's brain and to a second target region of the subject's brain based on the at least one phase of the signals from the source region to synchronize oscillations of the first target region and the second target region.

In accordance with another aspect of the disclosure, a method is provided for controlling synchrony in a plurality of brain regions of a subject that includes receiving signals from a source region of the subject's brain, determining at least one phase of the signals from the source region in a predetermined frequency band, delivering a first stimulation pulse to at least one target region of the subject's brain if a first phase of the signals from the source region is a first predetermined phase to control the synchronization of oscillations of the source region and the at least one target region and delivering a second stimulation pulse to the at least one target region if a second phase of the signals from the source region is a second predetermined phase to control the synchronization of oscillations of the source region and the at least one target region.

In accordance with another aspect of the disclosure, a system is provided for controlling synchrony in a plurality of brain regions of a subject. The system includes a signal detection module for receiving signals from a source region of the subject's brain, a signal generation module for generating at least one stimulation pulse, and a processor coupled to the signal detection module and signal generation module. The processor is programmed to receive the signals from the source region from the signal detection module, determine at least one phase of the signals from the source region in a predetermined frequency band, and control the signal generation module to generate at least one stimulation pulse based on the at least one phase of the signals from the source region and to deliver the at least one stimulation pulse to a target region to synchronize oscillations of the source region and the target region.

The foregoing and other advantages of the present disclosure will appear from the following description.

BRIEF DESCRIPTION OF THE DRAWINGS

The present invention will hereafter be described with reference to the accompanying drawings, wherein like reference numerals denote like elements. The patent or application file contains at least on drawing executed in color. Copies of this patent or patent application publication with color drawing(s) will be provided by the Office upon request the payment of the necessary fee.

DETAILED DESCRIPTION

Clinical treatments of brain conditions related to faulty brain circuit connectivity are limited due to the lack of established treatment paradigms. In particular, synchronized neural activity has been recognized as an important mechanism for communication between brain networks, including for attention, learning and memory formation. These networks, however, are often impaired in psychiatric disorders including depression, autism, post-traumatic stress disorder (PTSD), and obsessive compulsive disorder. Related networks are impaired in movement, sensory-motor, and neurodegenerative disorders, to which aspects of the present disclosure also apply. It is recognized herein that deep brain stimulation (DBS) can be a promising technique to help address these, and other disorders, due to due to its known safety and clinical translatability.

As such, the present disclosure provides systems and methods for controlling brain activity using stimulation, such as electrical stimulation. In particular, a novel approach is introduced whereby a synchrony between different regions of a subject's brain can be modified. Specifically, a stimulation pulse is delivered to one or more regions based on the electrophysiological state of another region. For example, the closed loop, phase locked method may deliver a stimulation pulse to a target region when the phase of oscillation of a source region is a predetermined phase or within a predetermined phase range. Repeatedly delivering stimulation pulses to a target region based on the phase of oscillation of a source region may entrain the oscillation of the target region to the source region and synchronize the oscillations of the two regions. Coherence or other indicators quantifying a connectivity between the two regions may be increased.

Figure 1:
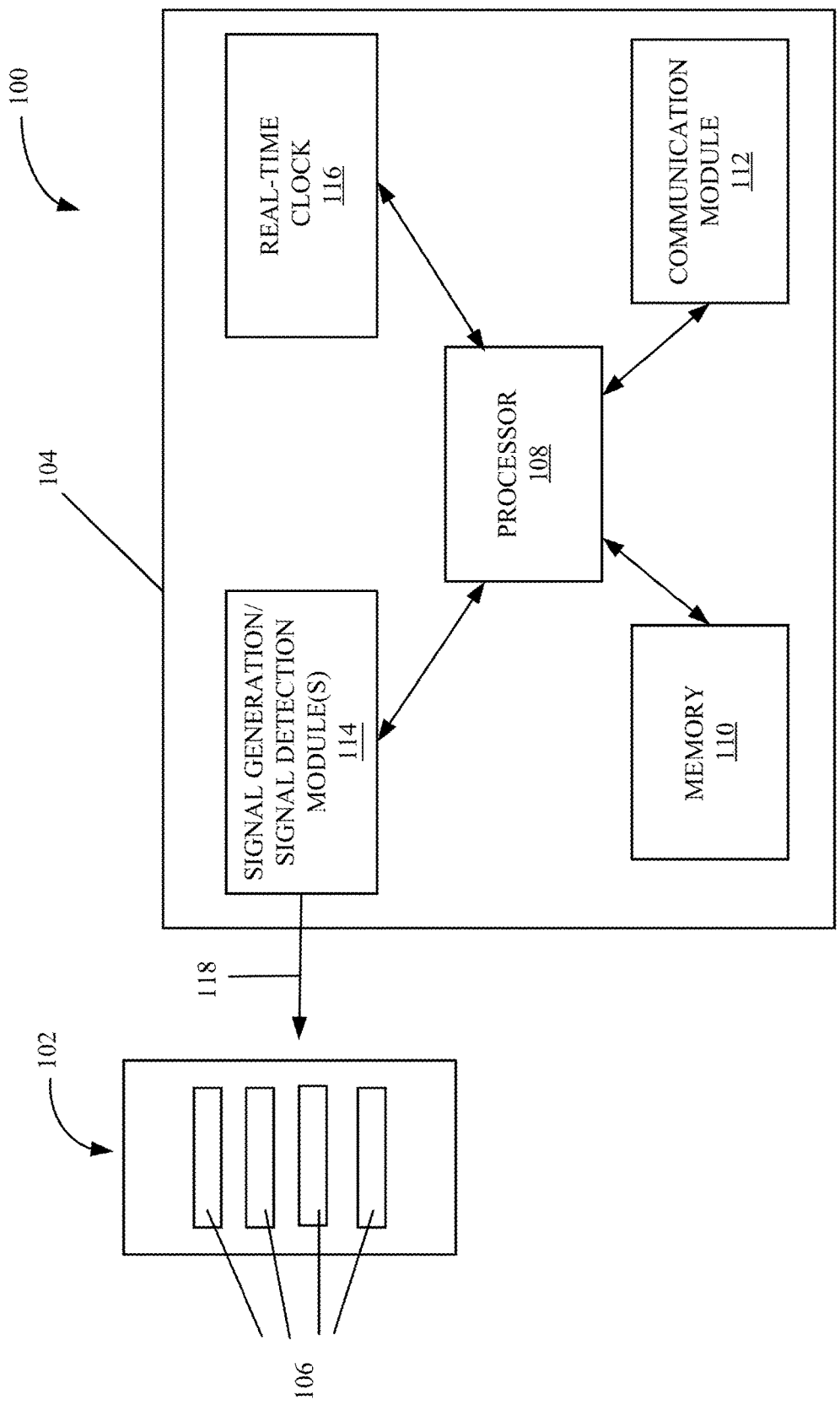
FIG. 1 is a block diagram of an exemplary stimulation system in accordance with an embodiment.

FIG. 1 is a block diagram of an exemplary stimulation system in accordance with an embodiment. As shown, the stimulation system 100 may generally include a stimulation assembly 102 and a controller 104 in communication with the stimulation assembly 102. The stimulation assembly 102 may include a number of stimulators 106 configured to deliver stimulations to control brain activity in the subject. The stimulators 106 may include various electrodes, or probes with electrical contacts, configured for delivering electrical stimulations to the subject. Examples, include micro electrodes, deep brain stimulation electrodes, electrocorticography (ECoG) arrays, electroencephalogram (EEG) electrodes, and the like. In some implementations, the stimulators 106 may be configured to provide other types of stimulations, including magnetic stimulations, for example using magnetic stimulation coils, and optical stimulations, for example, using optogenetic fibers, actuators, and the like. In addition, the stimulation assembly 102 may also include various detectors or sensors capable of measuring brain activity in the subject. Non-limiting examples, include electrical leads or contacts, magnetic detectors, optical detectors, and so forth. The stimulation assembly 102, or stimulators 106 therein, may be wholly or partially implanted in a patient's skull, scalp, or both. In other implementations, the stimulators 106, may be positioned on the subject but not implanted. Depending on the mode of stimulation, the stimulation assembly 102 may also utilize various methods and structures to support and couple the stimulators 106 and detectors to the subject.

The controller 104 may generally include a processor 108, a memory 110, such as flash or other type of memory, a communication module 112, signal generation/signal detection modules 114, a real-time clock 116, and optionally a power source (not shown). As shown, the controller 104 may also include various connections, or terminals 118 for transmitting signals generated by the signal generation module 114. Any or all of these elements may be implanted into a patient's body or carried/worn externally to the body, or some elements may be used in each configuration with an appropriate interconnection system.

In some implementations, the controller 104 may also include an input for accepting user selections, operational instructions and information, as well as an output or display for providing a report. Specifically, the input may include various user interface elements, such as a mouse, keyboard, touchpad, touch screen, buttons, and the like. The input may also include various drives and receptacles, such as flash-drives, USB drives, CD/DVD drives, and other computer-readable medium receptacles, for receiving various data and information. To this end, the input may also include various communication ports and modules, such as Ethernet, Bluetooth, or WiFi, for exchanging data and information with various external computers, systems, devices, machines, mainframes, servers or networks.

The processor 108 may be configured or programmed to perform a variety functions for operating the controller 104 using instructions stored in memory 112, in the form of a non-transitory computer readable medium, or instructions received via input. In some implementations, the processor 108 may control the sending and receiving of instructions and operational parameters (for example, via a wireless transcutaneous link in the communication module 112), the storage of the operational or stimulation parameters and instructions in memory 110, the transmission of the operational parameters to signal generators in the signal generation module 114, the selective triggering of the signal generators to provide electrical, and other stimulations, to various brain regions or tissues of a subject, as well as synchronizing various functions using the real-time clock 116. For instance, the processor 108 may communicate with the real-time clock 116 to determine the timing, phase lag, and synchronization of various stimulations. The processor 108 may also communicate with the real-time clock 116, as well as other hardware and digital logic circuitry, to accurately store activation times in memory 110 and provide activation counts. By way of example, the processor 308 can be a programmable microprocessor or microcomputer.

The signal generation module 114, in communication with the processor 108, may include a number of signal generators for providing activating signals to the stimulators 106. In some implementations, each of the stimulators 106 may be individually controlled using separate signal generators. The signal generators can be independently operated, either sequentially or concomitantly, by the processor 108, to provide stimulation signals with various intensities, frequencies, phases, pulse widths, durations and waveforms. In one embodiment, the signal generators may be controlled to provide stimulations in accordance with the methods described below with respect to FIGS. 2, 5 and 6. In addition, in some implementations, the signal generation module 114 may include an output sensing circuit to monitor contact output, as well as other fail-safe mechanisms. This may be desirable, for instance, in order to mediate timed switching for biphasic pulsing.

The signal detection module 114 may include various hardware, and be configured to detect brain signals acquired using the stimulation assembly 102. For instance, the signal detection module 114 can include various analog-to-digital converters, voltage/current meters, amplifiers, filters, and other elements. Signals from the signal detection module 114 may then be provided as input and processed by the processor 108. Alternatively, the signals may be stored in the memory 110 and subsequently accessed/processed by the processor 108.

In some aspects, the processor 108 may receive signals corresponding to brain activity in one or more regions of a subject's brain as input. The processor 108 may then analyze the signals, for example, to determine a synchrony between two or more regions, for example, by computing various metrics indicative of synchrony, such as coherence and others or to determine (or detect) a phase of oscillation of one or more regions. In some aspects, the processor 108 may receive such information from various input elements configured on the controller 104, as described, or alternatively from an external or remote device, computer or system, by way of the communication module 112. The processor 108 may also access a reference or database, as described, stored locally in the memory 110, or at storage location. In some implementations, the processor 108 may operate in an open-loop or a closed-loop fashion to control brain activity in a subject.

In some implementations, the controller 104, along with the stimulation assembly 102, may be part of a standalone stimulation system. Alternatively, the controller 104 may be a wearable or implantable unit that is programmable or configurable using an external device, computer or system. To this end, the communication module 112 may be configured to send and receive various signals, as well as receive power. Specifically, the communication module 112 may include an antenna, or an input-output wire coil, a receiver and transmitter, data converters, as well as other hardware components. As a non-limiting example, the receiver and transmitter may be configured to receive and transmit radio-frequency (RF) signals. In some implementations, the antenna may be configured for transcutaneous wireless two-way communication with an external wearable device, sending and receiving signals when the external wearable device is placed in close proximity. The communication signals may be transmitted through magnetic induction and include information for operating and/or programming the processor 108. For instance, the communication signals may include triggers or command signals for generating stimulations. In some aspects, transmitted signals may also be configured to power or recharge battery components powering the controller 104. The antenna may be connected to a receiver and transmitter, which in turn may be connected to serial-to-parallel and parallel-to-serial data convertors, respectively. Any information sent or received, as described, may then be processed by the processor 108.

As mentioned, the controller 104 may be powered by an internal and/or external power source. For example, an internal source may include a standard rechargeable battery, comparable to batteries used in implantable devices (e.g., pacemakers). Alternatively, or additionally, the internal power source may include a capacitor in combination with a regulator, such as a single ended primary inductor converter or dc-dc converter, that together can generate a constant current or voltage output for short periods of time. In some implementations, the capacitor may be charged by an external wearable device. As such, the controller 104 may include an induction coil, or thin, tightly wound wire that allows for RF telemetry and/or battery recharge by an external wearable device, configured either as part of the communication module 112, or as separate hardware. Other methods of charging may also be utilized.

Figure 2:
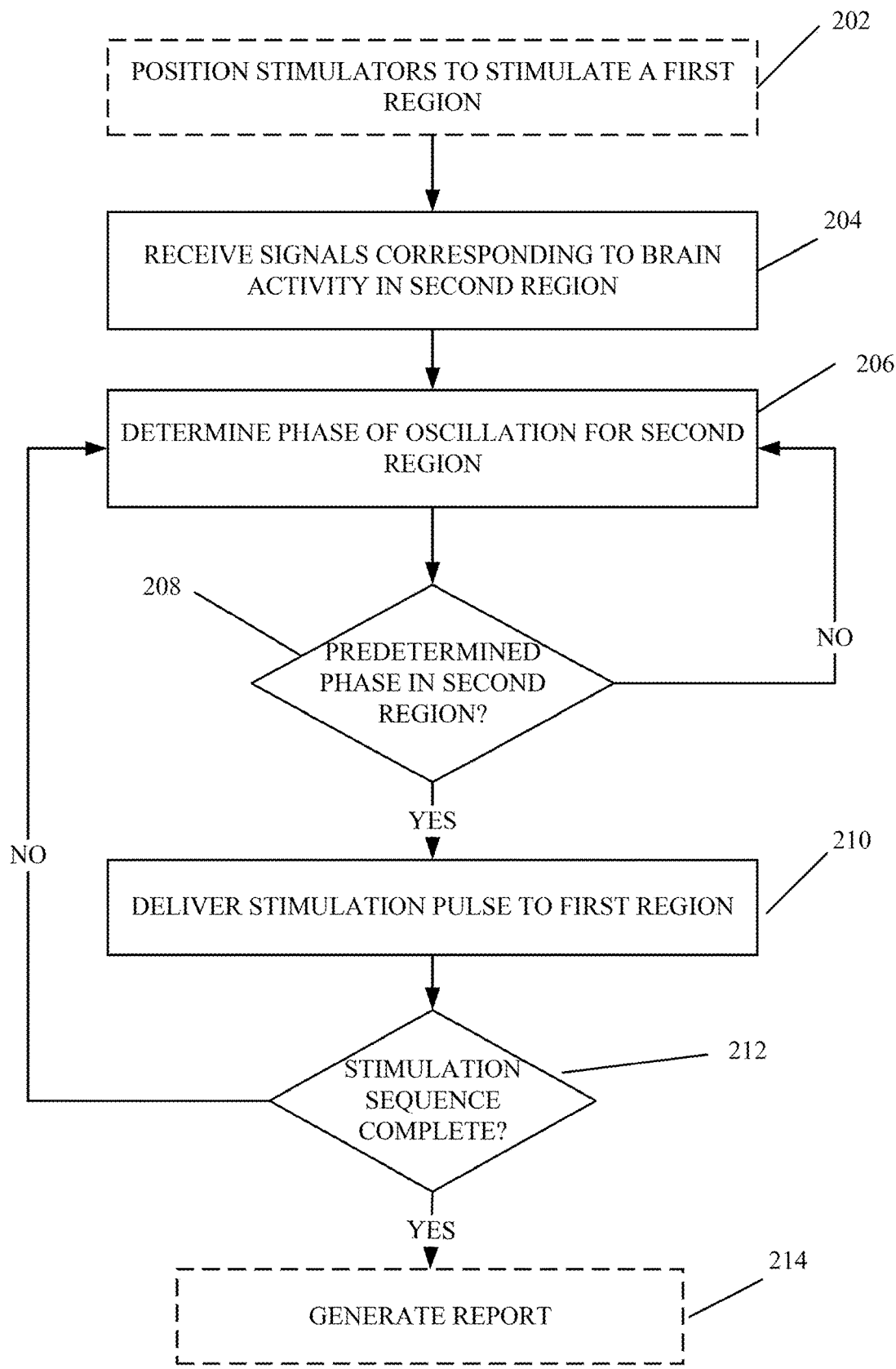
FIG. 2 illustrates a method for controlling synchrony in a plurality of brain regions in accordance with an embodiment.

FIG. 2 illustrates a method for controlling synchrony in a plurality of brain regions in accordance with an embodiment. The method may be carried out using any suitable device, apparatus or system, such as the stimulation system 100 described above with respect to FIG. 1. In some embodiments, the method may be implemented as a program, software or instructions stored in a memory such as a non-transitory computer readable medium or other storage location, that are executable, at least in part, by a processor or computer.

At block 202, the method may optionally begin with positioning stimulators to stimulate a subject's brain. For example, electrodes or optical fibers may be implanted in a subject's brain. In an embodiment, a number of stimulators (e.g., stimulators 106 shown in FIG. 1) may be positioned to simulate a first or target region of the subject's brain. In other implementations, the stimulators may be positioned on the subject but not implanted. In another embodiment, stimulators may be positioned to stimulate more than one target region of the subject's brain. However, positioning or implantation need not be carried out during execution of the process, but rather during a prior procedure or intervention.

Figure 3:
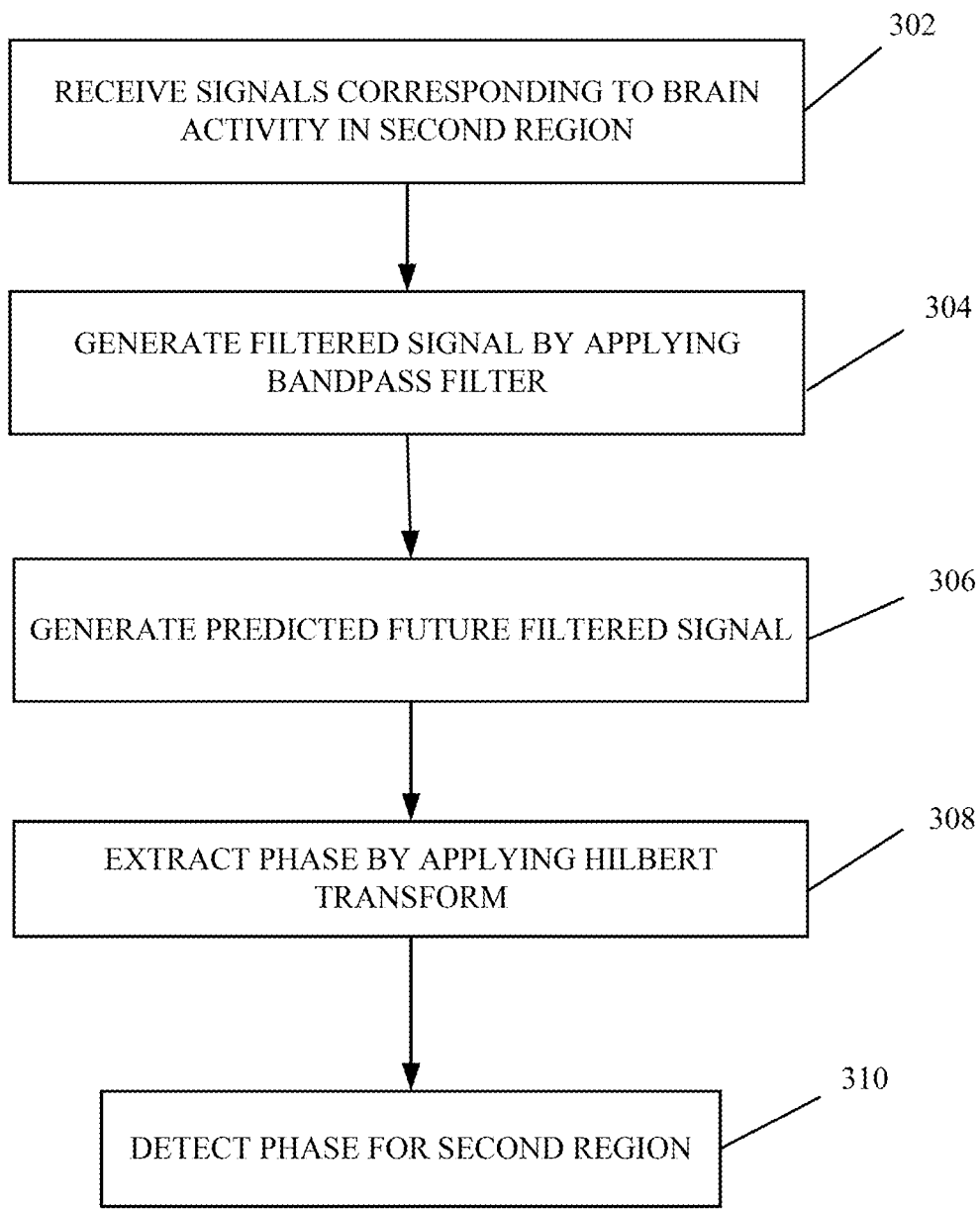
FIGS. 3 and 4 illustrate an exemplary method for determining the phase of oscillations in a region in accordance with an embodiment.
Figure 4:
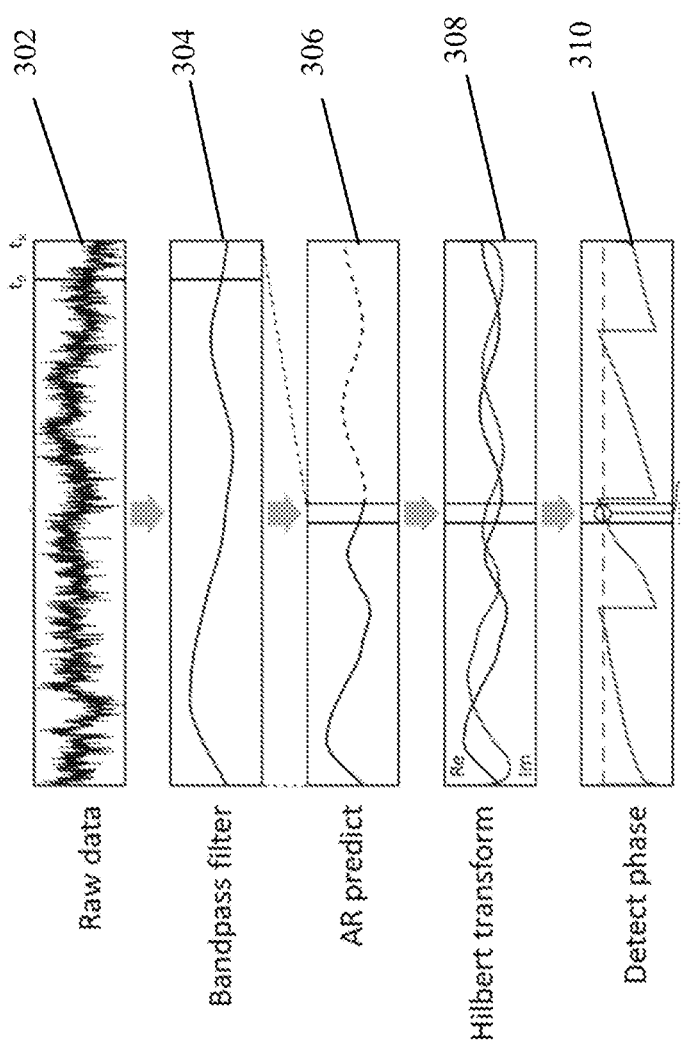

At block 204, signals corresponding to brain activity in a second or source region of the subject's brain are received, for example, by a signal detection module 114 (shown in FIG. 1) of the controller 104 (shown in FIG. 1). In an embodiment, the source signals are LFP signals acquired using electrodes positioned about a subject's brain. The source region and the target region may be separate regions of the brain and do not spatially overlap. At block 206, the received source signals are used to determine (or detect) the phase of oscillations of the second or source region in a predetermined frequency band. In one embodiment, the predetermined frequency band is a narrow frequency band. Various known methods may be used to detect the phase of oscillations such as, for example sliding-window Fourier transforms, all-pass Hilbert filters or latent-variable or state-space tracking methods. In one embodiment, a continuous phase estimation method is used to determine the phase of the source signals and to minimize error from the target region and variance in the stimulation phases. FIGS. 3 and 4 illustrate an exemplary method for determining the phase of oscillations in a source region in accordance with an embodiment. Referring to FIGS. 3 and 4, at block 302 signals corresponding to brain activity may be received from the source region as described above with respect to block 204 of FIG. 2. In an embodiment, LFP signals may be acquired from a region such as the prefrontal cortex (PFC) or the basolateral amygdala (BLA). At block 304, a band-pass filter is applied to the source signals to generate filtered source signals. At block 306, predicted future filtered signals are generated by using an autoregressive method on the filtered source signals. At block 308, phase information is extracted from the filtered signals (including both the filtered source signals and the predicted future filtered signals) by applying a Hilbert transform. In an embodiment, current samples from the filtered source signals are centered to minimize edge distortion. At block 310, the extracted phase information is used to detect the phase of oscillations for the current samples or time points for the source region. In an embodiment, the method may output a phase for each input sample ("continuously"), thereby reducing stimulation delay.

Returning to FIG. 2, at block 208 the determined or detected phase of the second region is monitored (e.g., peaks and troughs) in the predetermined frequency band. In one embodiment, the predetermined frequency band may be the frequency band in which a user wants to change oscillatory LFP coherence. If the phase detected is a predetermined phase or within a predetermined phase range, the process continues to block 210. At block 210, a stimulation pulse is delivered to the first or target region in response to detection of the predetermined phase or a phase value within a predetermined phase range. For example, the stimulation pulse may be delivered using the stimulators 106 as shown in FIG. 1. In an embodiment, a stimulation pulse may be delivered to more than one target region. For example, a stimulation pulse may be delivered to a first target region and a second target region. The stimulation pulse (e.g., electrical or other stimulation) may be monophasic or biphasic, with the pulse having any waveform or shape. The stimulation may be pulsed, continuous, or intermittent in the form of current or voltages, light, and so on, having various amplitudes, frequencies, periods, waveforms, durations, phases, polarities, and so on. In one embodiment, a user may select pre-programmed stimulation parameters such as target frequencies, intensities, durations, timings, and so on. Other information may be taken into consideration when setting the parameters of the stimulation such as a condition or disorder of the subject, targeted structures or regions in the brain, and properties (e.g., electrical, optical, magnetic) of such regions. In an embodiment, a user may also provide selections indicative of such targeted regions, tissue properties, subject disorder or conditions, and so on.

The stimulation pulse may be part of a stimulation sequence designed to provide more than one stimulation pulse over a selected or determined period of time. In an embodiment, the predetermined phase for the source region used to trigger delivery of a stimulation pulse to the target region is the same phase value or the same phase range for each stimulation pulse in the stimulation sequence. In another embodiment, the predetermined phase or predetermined phase range used to trigger delivery of a stimulation pulse to the target region may change or vary for each stimulation pulse. For example, the predetermined phase or the predetermined phase range for each stimulation pulse may be randomized as discussed further below with respect to FIG. 6. If the stimulation sequence is not complete at block 212, the process returns to block 206. If the detected phase is not the predetermined phase or within the predetermined phase range at block 206, the phase continues to be determined and monitored until the phase of the second region is the predetermined phase or within the predetermined phase range thereby triggering a stimulation pulse to be applied to the first or target region at block 210.

Figure 5:
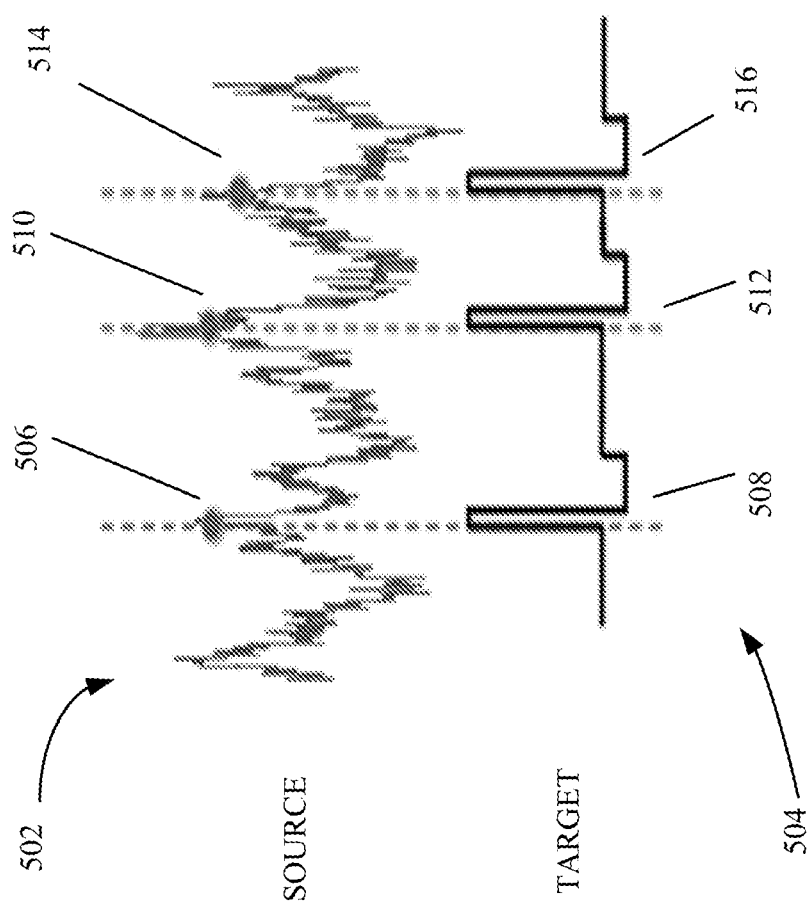
FIG. 5 illustrates timing of stimulation pulses in a target region based on a phase of oscillation in a source region in accordance with an embodiment.

FIG. 5 illustrates timing of stimulation pulses in a target region based on a phase of oscillation in a source region in accordance with an embodiment. In FIG. 5, the predetermined phase or the predetermined phase range used to trigger a stimulation pulse for a target region is the same for each stimulation pulse in a stimulation sequence 504. In an example, the phase of source signals 502 for a source region such as the prefrontal cortex (PFC) may be monitored in the theta frequency band (4-8 Hz) to determine when the phase of the source signal is at or near 180°. When the phase of oscillation is equal to or near 180° at a first predetermined phase occurrence 506, a first stimulation pulse 508 is delivered to the target region such as the basolateral amygdala (BLA). A second predetermined phase occurrence 510 triggers delivery of a second stimulation pulse 512 to the target region and a third predetermined phase occurrence 514 triggers delivery of a third stimulation pulse 516 to the target region. In an embodiment, each stimulation pulse may be a single electrical pulse (e.g., 90 μs and 100 μA). As discussed above, the stimulation sequence 504 may increase coherence.

Figure 6:
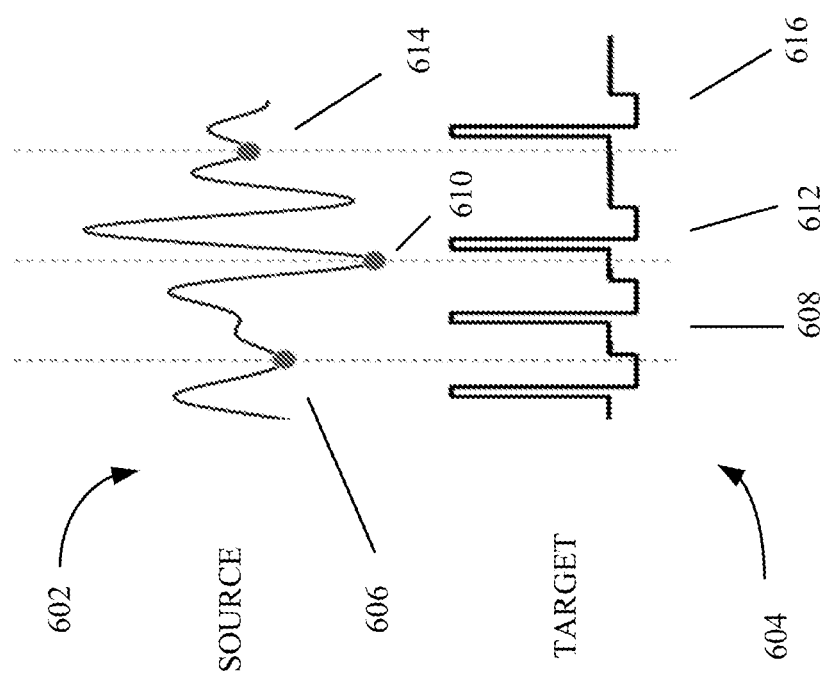
FIG. 6 illustrates timing of stimulation pulses in a target region based on a phase of oscillation in a source region in accordance with an embodiment.

FIG. 6 illustrates timing of stimulation pulses in a target region based on a phase of oscillation in a source region in accordance with an embodiment. In FIG. 6, the predetermined phase or the predetermined phase range used to trigger each stimulation pulse in the stimulation sequence 604 for a target region is randomized. In an example, the phase of source signals 602 for a source region such as the prefrontal cortex (PFC) may be monitored in the theta frequency band (4-8 Hz) to determine when the phase of the source signal is at or near a first predetermined phase 606. When the phase of oscillation is equal to or near the first predetermined phase 606, a first stimulation pulse 609 is delivered to the target region such as the basolateral amygdala (BLA). A second predetermined phase 610 triggers delivery of a second stimulation pulse 612 to the target region and a third predetermined phase 614 triggers delivery of a third stimulation pulse 616 to the target region. In an embodiment, each stimulation pulse may be a single electrical pulse (e.g., 90 µs and 100 µA). The stimulation sequence 604 based on randomized predetermined phases and phase locking may allow for bi-directional control of oscillatory synchrony. For example, coherence may be either increased or decreased.

Returning to FIG. 2, if the stimulation sequence is complete at block 212, a report may optionally be generated and displayed at block 214. The report may be in any form and include any information including any stimulations, parameters thereof, or measurements acquired from a subject. In some aspects, the report may include the selected stimulation sequence in the form of instructions, executable by a stimulation system. The report may include measurements such as, for example, local field potential (LFP) measurements, electroencephalogram (EEG) measurements, single-neuron measurements, multi-neuron measurements, spike measurements, optical measurements, sonic measurements and others. The report may also include various metrics of synchrony that may be generated based on one or more such measurements. The metrics of synchrony may include coherence, cross-correlations, multi-signal computations, principal-component computations, and so on. In one aspect, coherence between regions of the brain may be computed using respective LFP signals, which may then be used to determine a synchrony or a connectivity between the regions. The metrics of synchrony may be used to select parameters for further application of the methods for stimulation described herein.

Figure 7A:
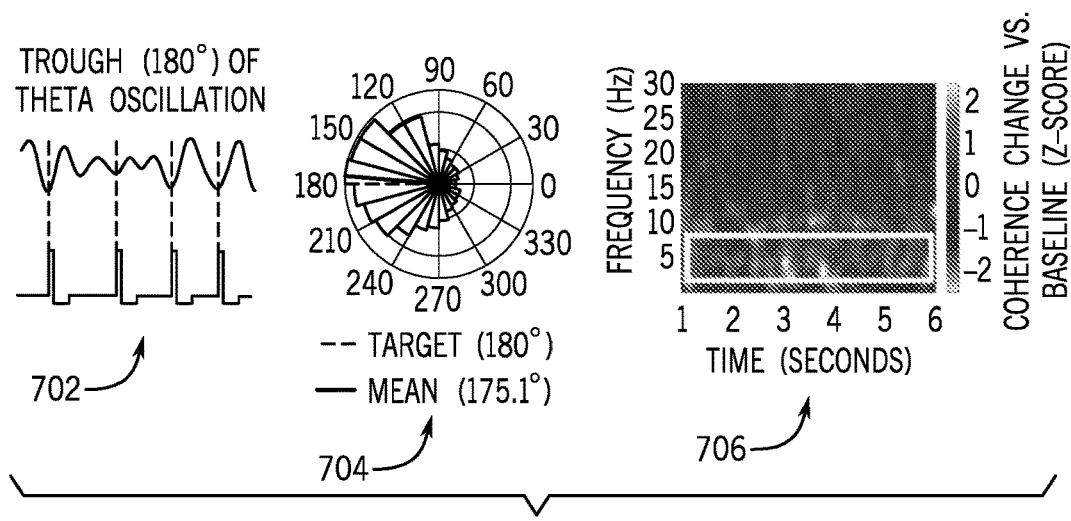
FIG. 7A shows example graphs illustrating results of using closed-loop, phase locked stimulations to control theta-band oscillations in an animal model in accordance with an embodiment.
Figure 7B:
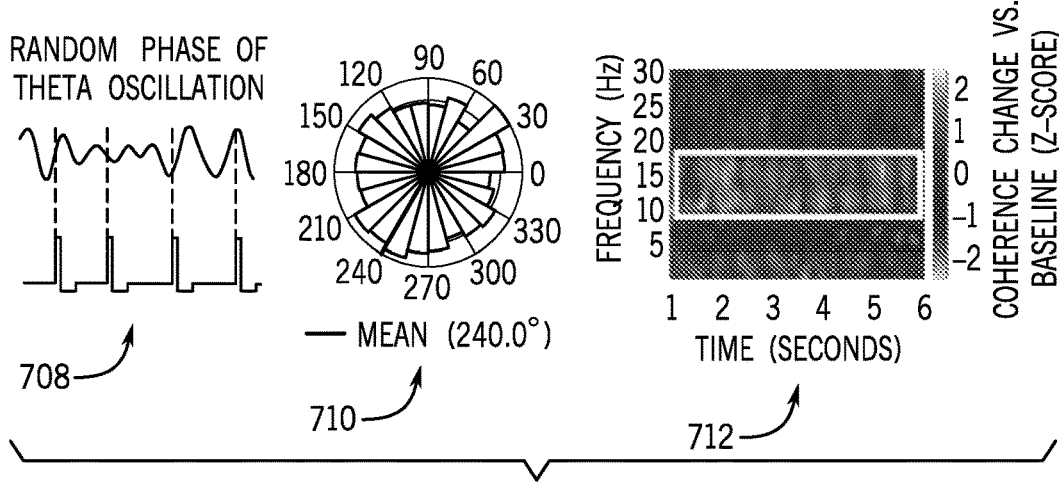
FIG. 7B shows example graphs illustrating results of using closed-loop, phase locked stimulations with a randomly selected phase for delivery of each pulse to control theta-band oscillations in an animal model in accordance with an embodiment.
Figure 7C:
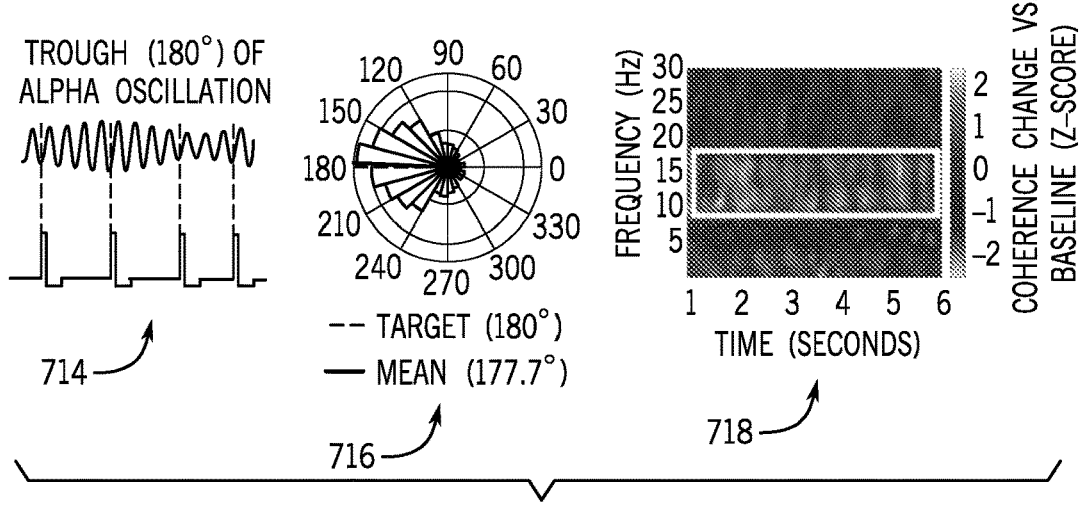
FIG. 7C shows example graphs illustrating results of using closed-loop, phase locked stimulation to control alpha-band oscillations in accordance with an embodiment.

By way of example, the present approach was utilized to alter oscillatory synchrony in brain activity of rodent models. FIGS. 7A-7C show example graphs illustrating results of using closed-loop, phase locked stimulations in an animal model in accordance with various embodiments. In the examples of FIG. 7A-7C, the source region was the prefrontal cortex (PFC) and the target region was the basolateral amygdala (BLA). LFP signals were acquired from both the source and target region. The phase detection method described above with respect to FIGS. 3 and 4 was used to continuously estimate the phase of oscillations in the PFC. In the example of FIG. 7A, the phase of oscillations were estimated in the theta-band and electrical stimulation pulses were delivered to the BLA when the phase of the oscillations in the PFC was at or near 180° as shown by the stimulation pattern 702. In the example of FIG. 7B, the phase of oscillation were estimated in the theta-band and electrical stimulation pulses were delivered to the BLA when the phase of the oscillations in the PFC was an angle randomly generated for each pulse as shown by the stimulation pattern 708. In the example of FIG. 7C, the phase of oscillations were estimated in the alpha-band and electrical stimulation pulses were delivered to the BLA when the phase of the oscillations in the PFC was at or near 180° as shown by the stimulation pattern 714. In each example of FIGS. 7A, 7B and 7C, a maximum of one stimulation pulse was delivered per second over a period of approximately 30 minutes for each session.

To evaluate the performance of the phase detection method used for the real-time estimation in the examples of FIGS. 7A, 7B and 7C, the LFP signals acquired from the source region was analyzed after each session with a non-causal bandpass filter and Hilbert transform to obtain a more accurate measurement of the phase in the frequency band of interest at each timepoint. Rose plots 704, 710, 716 show the distribution of the "offline" phase measurements at timepoints when the phase estimation method used in real-time signaled that stimulation pulses should be delivered (combined across sessions within each condition). In one implementation, stimulation pulses were delivered on every second such signal, namely those not included in the rose plots, to prevent electrical stimulation artifacts from impeding phase analysis at the other signal times. In one aspect, success of the phase-detection method may be indicated by the concentration of the phase distributions for sessions targeting 180° around the target phase.

FIGS. 7A, 7B and 7C also include a time-frequency plot 706, 712, 718, respectively, that shows the measured change in coherence between PFC and BLA after each session compared to a baseline before stimulation (averaged across sessions within each condition) for each example, respectively. In each plot 706, 712, 718, the frequency band of interest for that example is highlighted. The visible increase in coherence for the conditions targeting 180° (plots 706, 718) and the visible decrease in coherence when the predetermined phases were randomized (plot 712) indicate that the process in accordance with aspects of the present disclosure is controlling synchrony between the source and target brain regions. Whether the coherence between the source and target regions may depend on the method used for timing of the stimulation pulses based on the phase of the source region, namely, using the same predetermined phase for triggering each stimulation pulses or using a randomized phase for triggering each stimulation pulse.

As appreciated from description above, herein provided systems and methods utilize a novel approach and have a broad range of applications, including for treatment of patients with various neurological and psychiatric disorders. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for controlling synchrony in a plurality of brain regions of a subject, the method comprising:
receiving signals from a source region of the subject's brain;
determining at least one phase of the signals from the source region in a predetermined frequency band;
determining if the at least one phase of the signals from the source region is within a predetermined phase range; and
in response to the determination that the at least one phase of the signals from the source region is within the predetermined phase range, delivering at least one stimulation pulse to at least one target region of the subject's brain to synchronize oscillations of the source region and the at least one target region.

2. The method according to claim 1, wherein the at least one stimulation pulse entrains oscillations of the at least one target region to the source region.

3. The method according to claim 1, further comprising generating a report including synchrony information.

4. The method according to claim 1, wherein the predetermined phase range is a predetermined phase.

5. The method according to claim 4, wherein the predetermined phase is 180 degrees.

6. The method according to claim 4, wherein the at least one stimulation pulse is a stimulation sequence having a plurality of stimulation pulses and delivering at least one stimulation pulse to the at least one target region includes delivering a first stimulation pulse if a first phase of the signals from the source region is the predetermined phase and delivering a second stimulation pulse if a second phase of the signals from the source region is the predetermined phase.

7. The method according to claim 1, wherein the at least one stimulation pulse is a stimulation sequence having a plurality of stimulation pulses and delivering at least one stimulation pulse to the at least one target region includes delivering a first stimulation pulse if a first phase of the signals from the source region is within the predetermined phase range and delivering a second stimulation pulse if a second phase of the signals from the source region is within the predetermined phase range.

8. The method according to claim 1, wherein the at least one target region comprises a first target region and a second target region.

9. The method according to claim 1, wherein the source region and the at least one target region are separate regions and do not spatially overlap.

10. A method for controlling synchrony in a plurality of brain regions of a subject, the method comprising:
receiving signals from a source region of the subject's brain;
determining at least one phase of the signals from the source region in a predetermined frequency band;
determining if the at least one phase of the signals from the source region is within a predetermined phase range; and
in response to the determination that the at least one phase of the signals from the source region is within the predetermined phase range, delivering at least one stimulation pulse to a first target region of the subject's brain and to a second target region of the subject's brain to synchronize oscillations of the first target region and the second target region.

11. The method according to claim 10, wherein the at least one stimulation pulse entrains oscillations of the first target region and the second target region.

12. A method for controlling synchrony in a plurality of brain regions of a subject, the method comprising:
receiving signals from a source region of the subject's brain;
determining at least one phase of the signals from the source region in a predetermined frequency band;
delivering a first stimulation pulse to at least one target region of the subject's brain if a first phase of the signals from the source region is a first predetermined phase to control the synchronization of oscillations of the source region and the at least one target region; and
delivering a second stimulation pulse to the at least one target region if a second phase of the signals from the source region is a second predetermined phase to control the synchronization of oscillations of the source region and the at least one target region.

13. The method according to claim 12, wherein the first stimulation pulse and the second stimulation pulse increase coherence between the source region and the at least one target region.

14. The method according to claim 12, wherein the first stimulation pulse and the second stimulation pulse decrease coherence between the source region and the at least one target region.

15. A system for controlling synchrony in a plurality of brain regions of a subject, the system comprising:
a signal detection module for receiving signals from a source region of the subject's brain;
a signal generation module for generating at least one stimulation pulse; and
a processor coupled to the signal detection module and signal generation module, the processor programmed to:
receive the signals from the source region from the signal detection module;
determine at least one phase of the signals from the source region in a predetermined frequency band;
determine if the at least one phase of the signals from the source region is within a predetermined phase range; and
in response to the determination that the at least one phase of the signals from the source region is within the predetermined phase range, control the signal generation module to generate at least one stimulation pulse and to deliver the at least one stimulation pulse to at least one target region to synchronize oscillations of the source region and the at least one target region.

16. The system according to claim 15, wherein the at least one stimulation pulse entrains oscillations of the at least one target region to the source region.

17. The system according to claim 15, wherein the processor is further programmed to generate a report including synchrony information.

18. The system according to claim 15, further comprising at least one stimulator coupled to the signal generation module and the at least one target region, wherein the signal generation module is configured to control the at least one stimulator to deliver the at least one stimulation pulse to the at least one target region.

19. The system according to claim 15, wherein the predetermined phase range is a predetermined phase.

20. The system according to claim 19, wherein the predetermined phase is 180 degrees.

21. The system according to claim 20, wherein the at least one stimulation pulse is a stimulation sequence having a plurality of stimulation pulses and the processor further controls the signal generation module to deliver a first stimulation pulse if a first phase of the signals from the source region is the predetermined phase and to deliver a second stimulation pulse if a second phase of the signals from the source region is the predetermined phase.

22. The system according to claim 15, wherein the at least one stimulation pulse is a stimulation sequence having a plurality of stimulation pulses and the processor further controls the signal generation module to deliver a first stimulation pulse if a first phase of the signals from the source region is within the predetermined phase range and to deliver a second stimulation pulse if a second phase of the signals from the source region is within the predetermined phase range.

23. The system according to claim 15, wherein the at least one target region comprises a first target region and a second target region.

* * * * *